(12) United States Patent
Lazebnik

(10) Patent No.: US 8,956,301 B2
(45) Date of Patent: Feb. 17, 2015

(54) OPTIMIZATION OF LINES PER SECOND FOR MEDICAL DIAGNOSTIC ULTRASOUND CONTRAST AGENT IMAGING

(75) Inventor: Roee Lazebnik, San Jose, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 717 days.

(21) Appl. No.: 13/021,549

(22) Filed: Feb. 4, 2011

(65) Prior Publication Data

US 2012/0203112 A1 Aug. 9, 2012

(51) Int. Cl.
*A61B 8/00* (2006.01)
*A61B 8/08* (2006.01)
*A61B 8/14* (2006.01)

(52) U.S. Cl.
CPC . *A61B 8/481* (2013.01); *A61B 8/14* (2013.01); *A61B 8/5246* (2013.01); *A61B 8/54* (2013.01)
USPC ............................... 600/458; 600/437

(58) Field of Classification Search
CPC ............................... A61B 8/481; A61B 8/543
USPC .......................... 600/458, 437, 443
See application file for complete search history.

(56) References Cited

U.S. PATENT DOCUMENTS

| | | | |
|---|---|---|---|
| 6,110,120 A | 8/2000 | Holley et al. | |
| 6,494,841 B1 | 12/2002 | Thomas et al. | |
| 6,602,195 B1 | 8/2003 | Krishnan et al. | |
| 6,632,177 B1 | 10/2003 | Phillips et al. | |
| 6,638,228 B1 | 10/2003 | Brock-Fisher et al. | |
| 6,682,482 B1 | 1/2004 | Krishnan | |
| 7,780,602 B2 | 8/2010 | Hao et al. | |
| 2003/0092991 A1 | 5/2003 | Sehgal | |
| 2007/0081711 A1* | 4/2007 | Kim et al. | 382/128 |
| 2007/0276236 A1* | 11/2007 | Jong | 600/437 |

* cited by examiner

*Primary Examiner* — Rajeev Siripurapu

(57) ABSTRACT

Frame rate and/or line density are controlled in contrast agent medical diagnostic ultrasound imaging. The number of lines scanned per second (e.g., frame rate and/or line density) is set based on the differences in contrast agent response. Where the contrast agent response is changing rapidly, more frequent scanning and/or denser scanning is performed. Where the contrast agent response is not changing or changing slowly, less frequent scanning and/or less dense scanning is performed. By linking the number of scan lines per second of the scanning adaptively with the contrast agent response, the destruction of contrast agents may be reduced while providing information when needed for diagnosis.

15 Claims, 2 Drawing Sheets

OPTIMIZATION OF LINES PER SECOND FOR MEDICAL DIAGNOSTIC ULTRASOUND CONTRAST AGENT IMAGING

BACKGROUND

The present embodiments relate to contrast agent enhanced medical diagnostic ultrasound imaging. In particular, contrast agent imaging adapts over time.

Contrast-agent enhanced ultrasound (CEUS) is a common technique for visualization, diagnosis, and analysis of a variety of organs and pathologies. Contrast agents typically are gas-filled microbubble solutions, which are administered intravenously to a subject. As the contrast agents circulate throughout the subject's vascular system, the microbubbles serve as detectable acoustic reflectors. There are specific ultrasound pulse sequence combinations or types of scans that enhance microbubble detection. As the agents reach tissue, the agents perfuse into the tissue. The tissue is perfused at a rate or in a quantity of agent based, at least in part, on the health of the tissue. Unhealthy tissue (e.g., a tumor or other lesion) may uptake contrast agent to a different extent or rate than surrounding healthy tissues. A region of more substantial uptake may visually appear as a bright (hyper echoic) region compared to the surroundings.

Physiologic and pathologic conditions may be associated with specific contrast agent enhancement patterns. For example, a malignant lesion within the liver may enhance quickly (e.g., uptake at a greater rate or to a greater extent than surrounding tissue), but then "wash out" more quickly. In addition, certain patterns, such as outer to inner enhancement of a lesion or spokewheel like enhancement pattern, are associated with specific diagnoses.

For most contrast agents, the microbubbles disappear from circulation within a short period of time, typically less than 15 minutes. Ultrasound pulses utilized to interrogate the microbubbles may result in bubble destruction. In general, more intense ultrasound waves destroy more microbubbles. As the gas-filled microbubbles circulate through the lungs, their contents are released into the atmosphere, destroying the microbubbles. Microbubbles are also destroyed due to various forces experienced while traveling throughout the vascular system.

Because some enhancement patterns for diagnosis require several minutes to evolve, it is important that a sufficient quantity of microbubbles remain in circulation throughout the time course of a particular pattern. However, in order to observe the pattern, the tissue is monitored with ultrasound scanning fairly continuously. Thus, there is a tradeoff between the observation of microbubbles and their destruction during the observation process. The user may minimize microbubble destruction by maintaining a low mechanical index (MI) of the ultrasound beam, limiting the number of beams utilized to generate a given frame, and minimizing the duration of active imaging.

BRIEF SUMMARY

By way of introduction, the preferred embodiments described below include methods, systems, computer readable media, and instructions for controlling contrast agent medical diagnostic ultrasound imaging. The number of lines scanned per second (e.g., frame rate and/or line density) is set based on the differences in contrast agent response. Where the contrast agent response is changing rapidly, more frequent scanning and/or denser scanning is performed. Where the contrast agent response is not changing or changing slowly, less frequent scanning and/or less dense scanning is performed. By linking the number of scan lines per second of the scanning adaptively with the contrast agent response, the destruction of contrast agents may be reduced while providing information when needed for diagnosis.

In a first aspect, a method is provided for controlling contrast agent medical diagnostic ultrasound imaging. Ultrasound frames of data representing, at least in part, information from contrast agents are acquired. The ultrasound frames represent a region of a patient at different times. At least two of the ultrasound frames from the different times are compared. The comparing indicates a difference between the at least two of the ultrasound frames. A number of scan lines per second are altered for subsequently acquired ultrasound frames of data representing the information from contrast agents. The altering is a function of the difference. An image is generated from at least one of the subsequently acquired ultrasound frames.

In a second aspect, a non-transitory computer readable storage medium has stored therein data representing instructions executable by a programmed processor for controlling contrast agent medical diagnostic ultrasound imaging. The storage medium includes instructions for determining a level of similarity between data responsive to contrast agents in a region of a patient at different times, and setting a frame rate for further scanning of the region, the setting being a function of the level of similarity.

In a third aspect, a system is provided for controlling contrast agent medical diagnostic ultrasound imaging. A beamformer is configured to scan for contrast agents in a field of view. A contrast agent detector is configured to detect contrast agent information as a function of the scanning by the beamformer. A processor is configured to control frames rate, line density, or frame rate and line density of the scanning by the beamformer as a function of a rate of change of the contrast agent information.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Microbubble agent destruction is minimized automatically during contrast agent enhanced ultrasound (CEUS). Imaging frame rates and/or number of scan lines are optimized based on dynamic response from the contrast agents or scanning. The interaction of acoustic energy with microbubbles is reduced or minimized while maintaining a frame rate and image quality sufficient for evaluation.

The frequency of observation for diagnosis may depend on the response to the scanning. If the tissue or contrast agent response changes little from frame to frame, then only occasional imaging may be needed. During some phases of enhancement, very rapid changes occur. The sampling frequency is higher for these times. A dynamic frame rate adapts to the response from the scanning.

Figure 1:
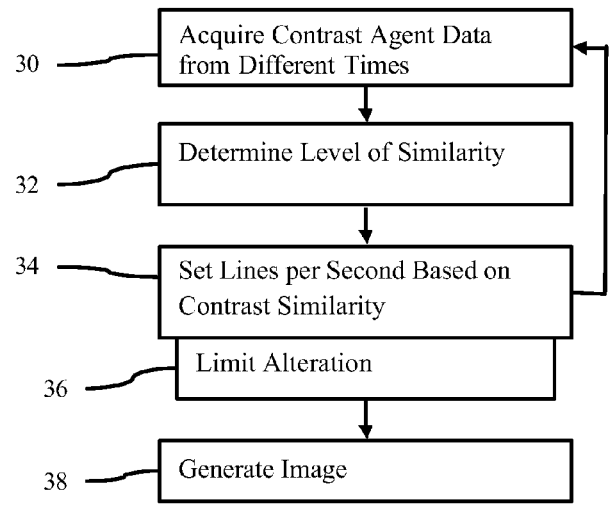
FIG. 1 is a flow chart diagram of a method for controlling contrast agent medical diagnostic ultrasound imaging according to one embodiment

FIG. 1 shows a method for controlling contrast agent medical diagnostic ultrasound imaging. The number of scan lines per second is dynamically adjusted based on image content to optimize contrast enhanced ultrasound imaging. The visualization, diagnosis, and/or analysis of a variety of organs and pathologies using CEUS may be made better by destroying contrast agents less when less information is needed and by increasing the information when appropriate.

Figure 3:
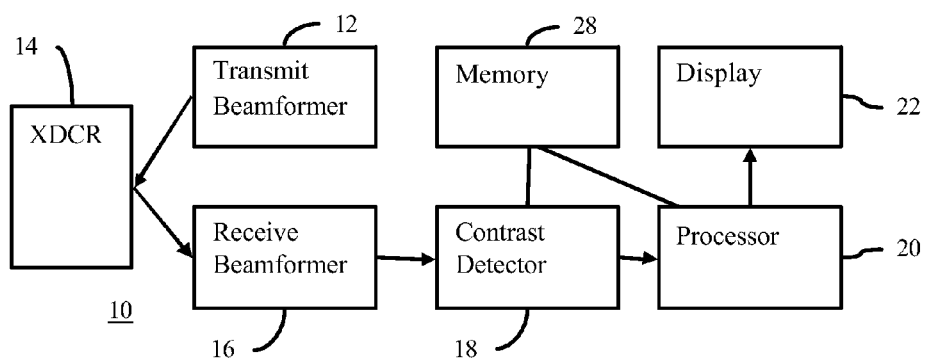
FIG. 3 is a block diagram of one embodiment of an ultrasound imaging system for controlling contrast agent medical diagnostic ultrasound imaging.

The method is implemented by the system 10 of FIG. 3 or a different system. The method is performed in the order shown or a different order. Additional, different, or fewer acts may be provided. For example, acts 36 and/or 38 are not provided.

For CEUS, the user initiates imaging, but automated initiation may be used. The ultrasound imaging system is configured for contrast agent imaging. Contrast agents are injected or otherwise provided within the patient or object to be scanned. The user or a robot positions the transducer relative to the patient so that the target is visualized within the field of view. For example, the liver is visualized. A lesion or region of the liver is placed within the field of view. Based on the spatial or temporal distribution of contrast agents at or in the lesion relative to surrounding tissue, information about the type of lesion or tumor may be determined. Any procedure may be used for studying the patient, at least in part, based on contrast agent response.

In act 30, ultrasound frames of data are acquired. The sequence is generated by acquiring frames of data with ultrasound. The frames of data are acquired in real time with live scanning. The sequence may be substantially continuous or periodic (e.g., acquired once or more every heart cycle).

Any frame rate and/or line density is used, such as a pre-configured, predetermined, adaptive, or user set frame rate. The user may choose settings, transducers, or other parameters from which the frame rate and/or line density result or are determined. Based on the settings, the scanning occurs at a given number of scan lines per second. By increasing or decreasing the frame rate, depth, line density, the number of scan lines per second scanned may be increased or decreased. Changing the temporal interval between frames or between scan lines changes the frame rate. Changing a line density between scans may or may not change the frame rate. Changes in line density with or without a change in frame rate may provide for a change in the number of scan lines per second. The scan lines used for the number are transmit, receive, or both transmit and receive lines. Simultaneous transmit beams or receive beams may be used. At least initially in the sequence, the number of scan lines per second may be set based on various factors not including feedback from the scanning.

The sequence includes frames of data representing a scanned region at different times. Each frame of data represents a same or overlapping region. The same number of scan lines is used for each frame, but the number of scan lines may vary from frame to frame. A frame of data represents the entire region at a given time (or range of times due to the time it takes to scan the region once or however many times to estimate the information for the region). Some frames may represent different regions, such as due to out-of-plane or in-plane motion of the transducer relative to the patient or internal movement of organs. Frames are acquired sequentially in an on-going or real time manner.

The region includes contrast agents or an area likely to include contrast agents after insertion of the agents. The contrast agents respond to ultrasound energies. Frames of contrast agent data are obtained. Some or all of the frames of data include information from contrast agents. The information may also include response from tissue or fluids.

Any contrast agent detection may be used. B-mode, Doppler, M-mode or other modes also used for tissue or fluid scanning may be used to detect contrast agents. Single or multiple pulse techniques may be used, such as sequentially transmitting to a same location with pulses 180 degrees out of phase and summing the resulting receive signals. Harmonic modes may be used, such as isolating information at even harmonics, the second harmonic, fractional harmonics, or the third harmonic. Filtering and/or combinations of receive signals from different transmissions may be used to isolate the desired harmonics.

In one embodiment, the information is obtained at a cubic fundamental of ultrasound signals. For example, ultrasound signals are transmitted in a plurality of pulses having at least two different amplitude levels and phases. To avoid or minimize destruction of the contrast agents, low amplitude transmissions (e.g., MI less than 0.1) are used. Signals responsive to the transmissions are combined, such as by summing or weighted summing. The combination provides data primarily responsive to contrast agents. Data is acquired at each spatial location of a region of interest in each frame of data.

Only one type of data is represented in the frames of data, such as data representing just contrast agents or responses from contrast agent and tissue. Alternatively, the frames of data represent different types of data, such as in a same frame or in different sets of frames. For example, frames of contrast agent data and separate frames of B-mode data are obtained. The B-mode information is generated separately from the contrast agent information. Alternatively, echo signals responsive to one of the pulses (e.g., the full or highest amplitude pulse) used for contrast agent information are used for B-mode detection. The B-mode or tissue information may include other information. For example, pulse sequences and/or filtering provide for tissue information from ultrasound signals at a fundamental, second harmonic, or both. The sequence of ultrasound frames of data represents, at least in part, information from contrast agents.

In act 32, a level of similarity between data responsive to contrast agents in a region of a patient at different times is determined. Two or more of the ultrasound frames are compared. The frames represent different, even if overlapping (e.g., using a moving window of receive signals for sequential frames generated by multiple pulse detection), times or at least partly different scans of the region. By comparing data from different frames, data representing the contrast agent perfusion of the region from different times is compared. The two frames are sequential, such as two most recently acquired frames. In other embodiments, the two frames are separated by one or more intervening frames of data. More than two frames may be compared, such as comparing to temporally filtered frames or determining similarity from any combination of multiple frames.

The comparison is of the entire frame. All of the data for each frame is compared. Alternatively, the comparison is for a region of interest in each frame. The region of interest is automatically or manually determined to represent a feature or locations of interest. Features or other extracted information may be compared in other embodiments.

The data may be aligned, such as using motion compensation, prior to comparison. Alternatively, the data of the frames is compared without motion compensation or aligning of features. For example, the region for comparison is indicated in each frame. By comparing regions, the information may be aligned. As another example, features are identified in each frame, so the data associated with the same features are compared. In yet another example, the frames are acquired and compared assuming no motion. The assumption may be accurate due to the user positioning the transducer for the desired field of view for acquiring each frame, due to the frame rate being sufficiently rapid to avoid movement, and/or due to the possible motion being acceptable.

The comparison indicates a difference between the ultrasound frames. The level of similarity is calculated. Any difference or similarity function may be used. For example, a mean difference of contrast agent data is determined. For each location, a difference between frames is calculated. The average of the differences across the frame is calculated as the difference. As another example, a correlation or minimum sum of absolute differences is calculated. In yet another example, a saliency function is calculated. Each frame is processed to identify one or more features, such as edges. Feature scores indicating edges, circular or other types of features of interest are calculated. A difference in scores may be calculated as the difference. Alternatively, the features identify the locations for which a difference is to be calculated. Other approaches to indicating similarity or difference may be used, such as mutual information or the mean difference (e.g., sum data for a region or frame in each frame and determine the difference between frame sums).

The ultrasound data may be processed before determining the difference. For example, the frames are spatially filtered. As another example, the frames are warped to remove the influence of regional tissue motion within the field of view.

The difference may be expressed as a scalar value representing difference or similarity. The difference may be an integer or other difference or similarity relative to one or more ranges. For example, the difference is compared to a threshold. If the difference is within one range defined by a pair of thresholds, different action may be taken. A difference of 0-3 in a normalized scale of 10 may indicate reducing the number of scan lines per second, with the difference of 4-6 indicating maintaining a same number of scan lines per second, and the difference of 7-10 indicating increasing the number of scan lines per second. Other mapping may be used with or without threshold comparison.

For contrast agent imaging, the difference is based, at least in part, on information from the contrast agents. To the extent the frames include tissue information as well, the tissue information may cancel due to the difference operation. Any differences are likely due to perfusion of the contrast agents.

In one example embodiment, the contrast agents have three general phases, an arterial phase, a portal phase, and a late phase. During the arterial phase, contrast agents rapidly flow to a region in arteries. This phase may last a few seconds, but may be longer or shorter. During the portal phase, the contrast agents perfuse in smaller vessels or arteries into tissues or organs. The portal phase may last minutes, but may be longer or shorter. During the late phase, the contrast agents are washed out of the tissue or organ. The late phase may last 3-5 minutes, but may be longer or shorter. The three phases are generally associated with different rates of change, the arterial phase being the most rapid and the late phase being the slowest. Other amounts of times, divisions of the process into fewer or more phases, different relative rates of change, or portions of the process used for diagnosis may be provided. For example, only spatial extent information is desired, so any late phase or washout information is not used.

In act 34, a number of scan lines per second for further scanning of the region is set. The number of scan lines per second corresponds to a frame rate, a line density per frame, or combinations thereof. For example, the frame rate is changed or set. The interval between frames may be increased or decreased. The frequency of the acquisition or scanning to acquire frames is set. The frame rate may be changed while keeping the number of scan lines per frame constant. The line density is constant. In alternative embodiments, the frame rate is changed, at least in part, by changing the line density. As another example, the line density per frame is changed or set with the frame rate being constant or different. The line density is based on transmit scan lines, receive scan lines, or both for acquiring a given frame. By increasing or decreasing the number of scan lines, the amount of time to scan a frame decreases or increases. The frame rate or frequency of frame acquisition is responsive to the line density. In other examples, a number of transmit and receive events per line may be set. The number of scan lines per second for a frame increases or decreases with change in the number of transmit or receive operations in a contrast agent imaging sequence.

The number is maintained the same or altered from previous scanning. An initial or predetermined number is replaced based on adaptive feedback about the difference in contrast agent response. In real-time operation, ultrasound frames are regularly, periodically, or occasionally acquired while examining a same patient in a same visit. The sequence of scans may be for a single study, such as associated with a given infusion of contrast agents (i.e., associated with a given infusion of a bolus of contrast agents or associated with an on-going infusion).

Once the number is set, the transmit and/or receive beamformation (e.g., scanning) is altered. By the time associated parameters are set, none, one, or further frames may have been acquired. The number is set for subsequent scanning, such as the next frame and/or other later frames in the sequence.

The number is set as a function of the level of similarity. Based on the difference between contrast agent response of frames from different times, the number is increased, decreased, or maintained. If the difference is increasing, the number of scan lines per second is increased. An increasing difference or a difference above a threshold amount (similarity below a threshold) indicates change between the frames. To better monitor the change, the number of scan lines per second is increased, such as increasing the frame rate. If the difference is decreasing, the number is decreased. A decreasing difference or a difference below a threshold amount (similarity above a threshold amount) indicates little to no change between frames. To reduce possible destruction of contrast agents, the number of scan lines per second is decreased. Where the difference is steady or within a tolerance, the number of scan lines per second is maintained.

The step size for any increase or decrease may be by increments. Alternatively, the step size is based on an amount of difference. In one embodiment, any difference is mapped to a given setting or amount of adjustment for a current setting. In another embodiment, the step size is proportional to the mean difference image-to-image using a linear scale ranging between predetermined minimum and maximum rate values.

In the example with arterial phase, portal phase and late phase, the rapid change associated with the arterial phase results in greater differences between sequential or other frames. As a result, the number of scan lines per second (e.g., frame rate) is increased, maintained if already high, decreased, or set at a higher level (e.g., 25-35 frames per second), depending on the initial settings. In the portal phase, the change is less than the arterial but more than in the late phase, so the number of scan lines per second (e.g., frame rate) is decreased or set at a lower level (e.g., 5-10 frames per second) as compared to the arterial phase. In the late phase, the rate of change is less than the portal phase, so the number of scan lines per second (e.g., frame rate) is decreased or set at an even lower level (e.g., 1-2 frames per second) as compared to the portal phase.

Figure 2:
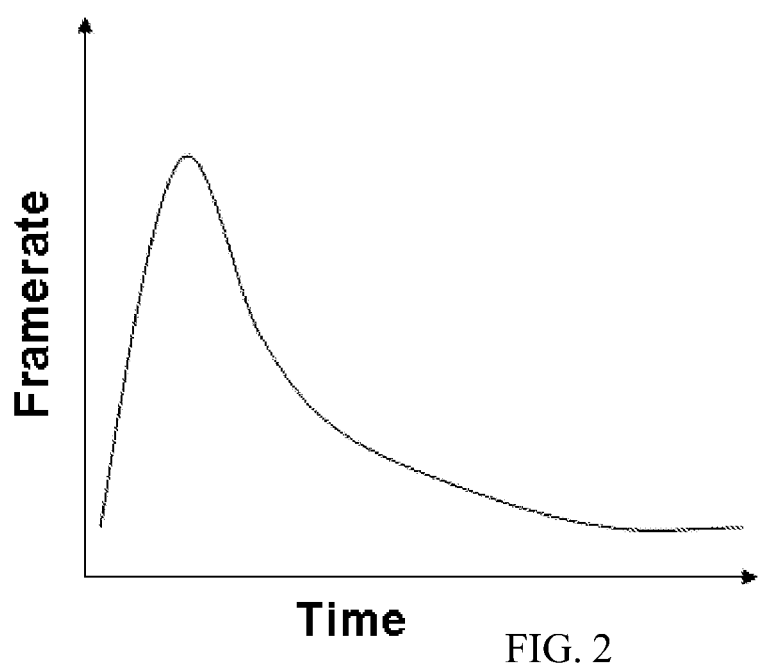
FIG. 2 is an example graphical representation of frame rate as a function of time.

In the example above, three frame rates (four including the initial rate) are used. Other numbers of frame rates may be provided, such as just two or more than three. Any mapping of the difference, as an absolute or as part of a rate of change, to the number of scan lines per second may be used. FIG. 2 shows an example frame rate set as a continuous function over time. The change in frame rate increments and then decrements. Any range of thresholds or any mapping function without thresholds for an amount of difference to change the number of scan lines per second may be used. For example, if sequential frames are sufficiently similar, the software reduces frame rate and/or line density. If sequential frames are sufficiently different, the software increases frame rate and/or line density.

In act 36, the altering of the number of scan lines per second is limited. The frame rate and/or line density may be changed up to a maximum and/or down to a minimum. The number of scan lines per second is restricted to be within a range. For example, where a continuous function or mapping of the difference to the number may continue to zero or infinity, the function or mapping is limited to a frame rate of at least one frame per second and of no more than thirty frames per second. The limit is set as an override or part of the mapping function, such as being incorporated into a look-up table. A pre-defined limit on the number of scan lines per second is used. Alternatively, no limit is provided.

In act 38, an image is generated from at least one of the subsequently acquired ultrasound frames. The image is formed as a function of the ultrasound frames of data. The image may be formed, at least in part, from signals of contrast agent response. Alternatively or additionally, the image is from subsequent scanning for B-mode or even non-contrast agent information. The contrast agent information is used to set the number of scan lines per second for acquiring contrast agent and/or other data, but may or may not be used for a given image. The image is grayscale, color, or combinations thereof.

More than one image may be generated. The setting occurs in an on-going manner. The acquiring of act 30, comparing of act 32, and altering of act 34 are performed repetitively during a contrast agent study of the patient. When a new frame is acquired, a difference from the immediately preceding or other reference frame is determined in act 32 and used to set the number of scan lines per second. The determining and setting are performed repetitively during the contrast agent study of the patient. Pairs or other groups of frames are compared for each repetition. One or more of the frames of the pair may be a frame also used for the previous repetition, such using a moving window so that different and more recently acquired sequential pairs of ultrasound frames are used in each repetition. Alternatively, the setting occurs periodically, such as every second or every heartbeat. In other embodiments, the difference determination and/or setting occurs in response to triggers.

FIG. 3 shows a system 10 for controlling contrast agent medical diagnostic ultrasound imaging. The system 10 includes a transmit beamformer 12, a transducer 14, a receive beamformer 16, a contrast agent detector 18, a processor 20, a display 22, and a memory 28. Additional, different, or fewer components may be provided. For example, a separate memory is provided for buffering or storing frames of data. As another example, the processor 20 is combined with or is part of the contrast agent detector 18, or the processor 20 is a beamformer controller.

The system 10 is a medical diagnostic ultrasound imaging system in one embodiment, but other imaging systems of the same (ultrasound) or different modality may be used. The system 10 provides real-time operation. In other embodiments, part or all of the system 10 is implemented in a computer or workstation. For example, acquired frames of data are streamed from the beamformers 12, 16 or transducer 14 and processed by a computer without beamformers 12, 16 or transducer 14. Software on the computer or workstation implements the control of frame rate or line density.

Now known or later developed systems may be used. For example, an existing ultrasound system is updated with a software modification to provide control in contrast agent imaging. As another example, contrast agent imaging software includes the adaptive control of the number of scan lines per second. In yet another embodiment, an ultrasound system is developed and sold with the capability.

The beamformer includes the transmit beamformer 12, the receive beamformer 16, or both the transmit and receive beamformers 12, 16. For both, the transmit beamformer 12 is a separate device or devices, at least in part, from the receive beamformer 16. Alternatively, both the transmit and receive beamformers 12, 16 include shared components.

The beamformer scans for contrast agents in a field of view. Using any scan format, such as linear, sector, or Vector®, the beamformer forms beams in the scan region. The formation of beams scans the region. Transmit beams are formed to generate echoes from tissue or fluid in the region. Receive beams are formed to generate signals representing the echoes. Different powers, foci, sequences, frequencies, or other characteristics of the beams may be used for creating and detecting response from contrast agents to the scanning.

The beamformer transmits and/or receives at a number of scan lines per second. By setting the line or scan repetition interval, depth of scan, number of scan lines per frame, or other characteristic, the number of scan lines per second may be changed. For example, 128 lines are transmitted in a sector format, with a depth of the field of view of 10 cm, and 128, 256 or other number of receive lines are formed in response. An interval between each transmission is set to minimize or avoid detecting reverberations from previous transmissions. The interval may be increased or decreased to change the rate. An interval between frames is set to control frame rate, such as being the same as the interval between scan lines or longer. To decrease the number of scan lines per second, the interval between frames is increased or the amount of time to acquire a frame is increased (e.g., more scan lines, greater depth, or greater interval between transmissions). To increase the number of scan lines per second, the opposite is done.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed. The transmit beamformer 12 may cause the beam to have a particular phase and/or amplitude. For example, the transmit beamformer 12 transmits a sequence of pulses associated with a given scan line or to adjacent scan lines. The pulses correspond to beams with different amplitudes and/or relative phases. In alternative embodiments, a single beam is used for any given scan line and/or beams with a same amplitude and/or relative phases are used.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. The elements connect with channels of the transmit and receive beamformers 12, 16. Alternatively, separate transducers 14 or elements are used for transmit and receive operation.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or other band.

Any desired sequence of transmit and receive operation may be used to obtain ultrasound information. For example, B-mode data may be obtained by scanning a region once. The B-mode data may be used for tissue imaging. Correlation or motion tracking may be used to derive fluid or contrast agent information from B-mode data. B-mode operation may provide contrast agent information with or without motion tracking. Doppler information may be obtained by transmitting sequences of beams along each scan line. A corner turning memory may be used to isolate tissue, contrast agents, and/or flow information from Doppler signals. Other now known or later developed modes may be used.

In one embodiment, the mode is a contrast agent imaging mode. Contrast agents may be imaged with typical B-mode or Doppler techniques. More contrast agent specific modes include isolating information at the second, even, odd, sub, or other harmonics, as such harmonics may more likely identify information from contrast agents. For example, a two pulse technique is used. The pulses have a same amplitude, but different phase. By summing the response, information associated with even harmonics is identified. As another example, the transmit beams are of the same phase and amplitude, but the received responses are subtracted from each other. Filtering may alternatively be used. Alternatively or additionally, relative phasing is provided in the receive processing.

In one embodiment, the transmit sequence is controlled to generate echo signals responsive to the cubic fundamental. The beamformer 12 is operable to transmit a plurality of pulses having at least two different amplitude levels and at least two of the plurality of pulses having opposite or different phases. Transmitter power can be varied in any suitable manner, as for example by adjusting the voltage applied to individual transducer elements, or by adjusting the number of transducer elements (or transmit aperture) used to form a particular pulse.

For obtaining ultrasound data at the cubic fundamental, the receive beamformer 16 includes line memories and a summer or a filter to combine signals responsive to the transmissions. The line memories or buffers can be formed as physically separate memories, or alternately can be formed as selected locations in a common physical device. The beamformed signals are stored in the line memories or buffers and then weighted and summed in a weighted summer. Weighting values for both amplitude and phase are used in the weighted summer. The memories and the summer can be implemented using analog or digital techniques. The weighted summer forms a composite output signal by weighting the separate beamformed receive signals. The composite output signal for a given spatial location is a sample associated with the cubic fundamental response.

Obtaining cubic fundamental information is disclosed in U.S. Pat. No. 6,494,841, the disclosure of which is incorporated herein by reference. Any of the transmit sequences and receive combinations disclosed therein may be used for obtaining cubic fundamental information. Other transmit sequences and receive combinations for obtaining cubic fundamental information may be used, such as disclosed in U.S. Pat. Nos. 6,602,195, 6,632,177, 6,638,228 and 6,682,482, the disclosures of which are incorporated herein by reference. In general, a sequence of pulses with different amplitudes and phases are transmitted. Using amplitude change or different amplitudes without different phases may also be used to obtain cubic fundamental information. By combining received signals responsive to the sequence, a sample including cubic fundamental information is obtained. The cubic fundamental information is highly specific to ultrasound contrast agents since contrast agents produce cubic response and the transducer and tissue produce very little cubic response. The information provides tissue clutter rejection, allowing for imaging more specific to contrast agents. For example, small vessels within tissue may be more easily imaged or identified using cubic fundamental information.

The contrast agent detector 18 is a B-mode detector, Doppler detector, pulsed wave Doppler detector, separate contrast agent detector, correlation processor, Fourier transform processor, application specific integrated circuit, general processor, control processor, field programmable gate array, digital signal processor, analog circuit, digital circuit, combinations thereof, or other now known or later developed device for detecting information for display from beamformed ultrasound samples. The contrast agent detector 18 detects contrast agent information as a function of the scanning by the beamformer. The receive signals generated in response to the transmitting are detected. The detected receive signals represent, at least in part, response of contrast agents.

In one embodiment, the contrast agent detector 18 implements a fast Fourier transform from a plurality of samples representing a same region or gate location. Each of the samples is responsive to cubic fundamental so that a pulsed wave Doppler display may be generated from cubic fundamental information. Any of the contrast agent detectors in the patents reference above may be used. Other components may be used for a contrast agent detector. For example, B-mode detection is provided. As another example, a filter combines information from different transmissions to enhance or better isolate the response from contrast agents (e.g., second harmonic or cubic fundamental). The filter obtains information primarily at a cubic fundamental or other frequency band of the transmitted ultrasound signals. Any detection of the signals is then performed, such as determining the power or intensity of the combined signals.

The system 10 may also include a B-mode and/or Doppler detector in a parallel track. The B-mode detector operates on the same or different beamformed samples to detect tissue, contrast agent, or tissue and contrast agent response. For example, one receive beam for each spatial location from the sequence of receive beams used for cubic fundamental isolation is applied to the B-mode detector for imaging primarily tissue information. The Doppler detector uses a sequence of receive signals from the same location to estimate velocity, variance, or power.

The contrast agent detector 18 and/or other detectors outputs frames of ultrasound data. The frames of data are formatted in an acquisition format (e.g., polar coordinate), a display format (e.g., scan converted into a Cartesian coordinate format or an image), or other format. Each frame of data represents a one, two, or three-dimensional scanned region, such as substantially the entire region to be imaged (substantially accounting for patient or transducer motion). The frames of data include a single or multiple types of data. For example, one frame of data includes just contrast agent information. As another example, one frame of data includes contrast agent information for some spatial locations and another type of information (e.g., B-mode or Doppler) for other spatial locations. Different types of data may be provided in the same frame for a same spatial location. In another example, the different types of data are provided in different frames of data.

The processor 20 is an application specific integrated circuit, correlation processor, Fourier transform processor, general processor, control processor, beamformer controller, field programmable gate array, digital signal processor, analog circuit, digital circuit, combinations thereof, or other now known or later developed device for controlling frames rate, line density, or frame rate and line density of the scanning by the beamformer. The number of scan lines per second is controlled as a function of a rate of change or difference of the contrast agent information. The processor 20 receives the frames of data to determine the number of scan lines per second to use.

The processor 20 performs dynamic throttling of framerate and line density during contrast enhanced ultrasound imaging. The throttling is based on frame-to-frame image analysis differences. The contrast agent information acquired at different times is compared. A difference in contrast agent information indicates the rate or amount of change. By determining the similarity between contrast agent response acquired at different times, the occurrence of significant change in contrast agent information is provided.

The processor 20 controls the number of scan lines per second to minimize acoustic rupturing of the microbubble agent while maintaining sufficient diagnostic quality. Control signals are provided to the beamformer, beamformer settings are selected or output, or other control is provided for setting the frame rate, line density, depth, line interval, or other scan characteristic for the number of scan lines per second.

For example, where change is occurring, the frame rate and/or line density is increased to provide possibly diagnostic information at a higher spatial and/or temporal resolution. Where little or no change is occurring, the frame rate and/or line density is decreased to avoid bubble destruction. Thresholds may be used for the adjustment. The processor 20 reduces the frame rate, line density, or both frame rate and line density where the rate of change is below a threshold. The processor 20 increases the frame rate, line density, or both frame rate and line density where the rate of change is above the threshold. The reduction or increase may be made by setting any one or more characteristics of the scan or beamformer. The values of the setting may be calculated from a function or may be looked-up from a table.

The increase or reduction may be performed in increments, such as restricting the rate or amount of change of the number of scan lines per second. Alternatively, the increase or reduction changes based on the difference where larger differences between contrast agent response indicates a greater difference in the number of scan lines per second.

By setting the characteristics of the beamformer scan, the processor 20 controls the frame rate, line density, or frame rate and line density. The control occurs during an examination of a patient, such as during a given visit of the patient to the sonographer or for a given infusion of contrast agents. Due to the control, different frame rates and/or line densities are used at different times in the examination. The different frame rates and/or line densities are based on differences in the contrast agent information from the scanning immediately prior to setting the frame rate or scanning during the examination.

The processor 20 may also include a scan converter, alpha blending buffer, frame buffer, memory, processor, adder, or other device for generating an image from one or more frames of data. Images may be generated for each frame of contrast agent data. The images are generated at a rate corresponding to the frame rate. The images may be generated at greater or lesser rates than the scanning rate, such as using interpolation or filtering between frames to increase an apparent frame rate. Spatial interpolation or filtering may be used to increase or decrease spatial resolution relative to the scanning resolution. One, two, or three-dimensional imaging may be used.

The display 20 is a CRT, monitor, LCD, flat panel, projector or other display device. The display 20 receives display values for displaying an image. The display values are formatted as a one-dimensional image, two-dimensional image, or three-dimensional representation. In one embodiment, the display values are for contrast agent information. A sequence of images showing contrast agent response over time is generated. The contrast agent information may include or be overlaid on tissue response, such as a B-mode image.

One image may be generated as a function of frames of data acquired at different times, such as a time intensity curve (TIC) or maximum intensity projection (MIP) image. An image of the combined frames of data output from the contrast agent detector is generated. As additional frames of data are acquired and selected, the image may be updated.

The sequence of images or a given image may show a temporal and/or spatial distribution of contrast agents. For example, a spokewheel response where the contrast agent accumulates in one location and then has accumulation in a radiating spoke or spider web pattern may indicate a focal nodular hyperplasia. As another example, peripheral nodular enhancement where contrast agents accumulate at the edges and then more rapidly fills in a lesion may indicate a hemangioma. In yet another example, a late occurring wash-out as compared to surrounding healthy tissue may indicate a malignant lesion.

One or more calculations may also be displayed. For example, the frame rate and/or line density is displayed. As another example, wash-in and/or wash-out times for one or more regions of interested are shown in a graph or calculated from the contrast agent information and displayed.

The beamformer, contrast agent detector 18 and/or processor 20 operate pursuant to instructions. The memory 28 is a computer readable memory. A computer readable storage medium stores data representing instructions executable by one or both of these programmed processors for controlling contrast agent medical diagnostic ultrasound imaging. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for controlling contrast agent medical diagnostic ultrasound imaging, the method comprising:
    acquiring ultrasound frames of data representing, at least in part, information from contrast agents, the ultrasound frames representing a region of a patient at different times;
    comparing at least two of the ultrasound frames from the different times, the comparing indicating a scalar value of a difference between same locations of the region represented in the at least two of the ultrasound frames;
    altering a number of scan lines per second for subsequently acquired ultrasound frames of data representing the contrast agents, the altering being based on the scalar value of as a function of the difference, wherein altering results in decreasing the number from a first value for an arterial phase to a second value for a portal phase and from the second value to a third value for a late phase, the portal phase being after an arterial phase and before the late phase; and
    generating an image from at least one of the subsequently acquired ultrasound frames.

2. The method of claim 1 wherein acquiring comprises scanning the region with ultrasound at the number of scan lines per second, wherein comparing comprises determining that the difference is above a threshold, and wherein altering comprises increasing the number of scan lines per second for subsequent scanning.

3. The method of claim 1 wherein altering comprises altering a frame rate.

4. The method of claim 1 wherein altering comprises altering a line density per frame.

5. The method of claim 1 further comprising limiting the altering to a minimum value, maximum value, or both minimum and maximum values for the number.

6. The method of claim 1 wherein comparing comprises calculating a difference of the information for just the contrast agents.

7. The method of claim 1 wherein altering comprises increasing the number where the difference is increasing and decreasing the number where the difference is decreasing.

8. The method of claim 1 wherein comparing comprises comparing the at least two ultrasound frames, the at least two ultrasound frames comprising sequential frames, wherein the acquiring, comparing and altering are performed repetitively during a contrast agent study of the patient.

9. In a non-transitory computer readable storage medium having
    stored therein data representing instructions executable by a programmed processor for controlling contrast agent medical diagnostic ultrasound imaging, the storage medium comprising instructions for:
    determining a level of similarity between data of detected contrast agents in a region of a patient at different times, the determining cancelling information from tissue from the level of similarity, and wherein the detected contrast agents are detected using contrast agent detection separate from B-mode detection of tissue information; and
    setting a frame rate for further scanning of the region, the setting being a function of the level of similarity.

10. The non-transitory computer readable storage medium of claim 9 wherein determining the level of similarity comprises determining that a difference is above a threshold, and wherein setting comprises increasing the frame rate for subsequent scanning.

11. The non-transitory computer readable storage medium of claim 9 wherein setting comprises altering the frame rate with a constant line density per frame.

12. The non-transitory computer readable storage medium of claim 9 wherein setting comprises altering a line density per frame such that frames are acquired at a different frequency.

13. The non-transitory computer readable storage medium of claim 9 further comprising limiting the frame rate to a minimum value, maximum value, or both minimum and maximum values.

14. The non-transitory computer readable storage medium of claim 9 wherein setting comprises increasing the frame rate where the level of similarity is decreasing and decreasing the frame rate where the level of similarity is increasing.

15. The non-transitory computer readable storage medium of claim 9 wherein determining comprises comparing at least a pair ultrasound frames from scans at the different times, wherein the determining and setting are performed repetitively during a contrast agent study of the patient, the pair for each repetition being different and for more recently acquired sequential ultrasound frames.

* * * * *